United States Patent [19]

Klem et al.

[11] Patent Number: 5,424,440
[45] Date of Patent: Jun. 13, 1995

[54] FLUORESCENT BENZOTHIAZOLE DERIVATIVES

[75] Inventors: Robert E. Klem, San Luis Obispo; William Marvin, Los Osos, both of Calif.

[73] Assignee: JBL Scientific, Inc., San Luis Obispo, Calif.

[21] Appl. No.: 158,167

[22] Filed: Nov. 24, 1993

Related U.S. Application Data

[63] Continuation of Ser. No. 999,183, Dec. 28, 1992, abandoned, which is a continuation of Ser. No. 216,896, Jul. 8, 1988, abandoned.

[51] Int. Cl.$^6$ ............................................. C07D 277/68
[52] U.S. Cl. .................................. 548/114; 548/156; 548/178; 536/17.3
[58] Field of Search ................. 548/114, 156, 178; 536/17.3

[56] References Cited

U.S. PATENT DOCUMENTS

| | | | |
|---|---|---|---|
| 3,741,876 | 6/1973 | Guilbault | 195/103.5 R |
| 4,307,187 | 12/1981 | Ikenoue et al. | 430/619 |
| 4,456,599 | 6/1984 | Woltersdorf | 548/114 X |
| 4,528,267 | 7/1985 | Calenoff et al. | 435/7 |
| 4,668,623 | 5/1987 | Kinnunen et al. | 435/19 |
| 4,705,861 | 11/1987 | Fürstenwerth | 548/178 |
| 4,708,810 | 11/1987 | Askew et al. | 252/50 |
| 4,910,211 | 3/1990 | Imamura et al. | 548/178 X |
| 5,035,999 | 6/1991 | Geiger et al. | 435/23 |
| 5,098,828 | 3/1992 | Geiger et al. | 435/7.72 |

FOREIGN PATENT DOCUMENTS

| | | |
|---|---|---|
| 0024525 | 3/1981 | European Pat. Off. |
| WO87/02667 | 5/1987 | WIPO . |

OTHER PUBLICATIONS

Cano et al., Biotechniques 12(2):204–267 (1992).
Kerkhof, Anal. Biochem. 205:359–364 (1992).
Cherry et al., Genomics 20:68–74 (1994).
Suzuki, et al., Tetrahedron 28:4057–4082 (1972).
White et al, JACS, vol. 88, No. 9 (May 1966) pp. 2015–2019.
Suzuki et al, Chemical Abstracts, vol. 77 (1972) 114294u.
Suzuki et al, Chemical Abstracts, vol. 78 (1973) 71982t.
Bowie, L. J., Methods of Enzymology 57:15–30 (1978).
DeLuca, M. and McElroy, W. D., Methods in Enzymology, LVII:3 et seq. (1978).
Faure, R., et al. Org. Magn. Reson. 11:1617–1627 (1978).
Rasmussen, H. N., Methods in Enzymology, LVII:2-8–50 (1978).
White, E. H., et al., J. Org. Chem., 43(12):2366–2369 (1978).
Cornish, C. J., et al., Amer. J. Clin. Pathol., 53:68–76 (1970).
Darrah, P. R., and Harris, P. J., Plant and Soil 92:81–88 (1986).
Fernley, H. N., and Walker, P. J., Biochem. J. 97:95 (1965).
Hashimoto, S., et al., Bunseki Kagaku 32:E177–E184 (1983).
Massoom, M. and Worsfold, P. J., Analytica Chimica Acta, 179:217–223 (1985).
Sherman, W. R., and Robins, E., Analytical Chemistry, 40(4):803–805 (1968).
Tiffany, T. O., Clin. Chem. 19(8):871–882 (1973).
Guilbault, G. G. and Sadar, S. H., Analytical Letters, 1(5):333–345 (1968).

(List continued on next page.)

Primary Examiner—Richard L. Raymond
Attorney, Agent, or Firm—Lyon & Lyon

[57] ABSTRACT

Novel benzothiazole derivatives having a fluorescence inhibiting group linked by an enzyme cleavable bond and methods for their synthesis are provided. Upon cleavage of the enzyme-cleavable bond, a strongly fluorescent reaction product is produced. These compounds may be used to detect enzymatic activity. The fluorescent reaction products are detectable at an attomolar level using a fluorometer.

12 Claims, 11 Drawing Sheets

OTHER PUBLICATIONS

Wolfbeis, O. S., et al., Mikrochimica Acta (Wien) I:3-89–395 (1985).
Lee, Ching–Li, et al., Cancer Res., 38:2871–2878 (1978).
Vaughn, A., et al., Analytical Chem., 43(6):721–724 (1971).
Hill, H. D., et al., Analytical Biochem., 24:9–17 (1968).
Waters, M. D., et al., Biochim. Biophys. Acta, 159:420–422 (1968).
Bretaudiere, J. and Spillman, T., Methods of Enzymatic Analysis, Bergenmeyer, H., ed., IV:75–89 (1984).
Tietz, N. W., Clin. Chem., 29(5):751–761 (1983).
Guilbault, G. G., J. of Research, 76A(6):607–612 (1972).
Henderson, A. R. and Nealon, D. A., Clinical Enzymology in Clinical Biochem. Rev., pp. 187–234 (1982).
Shah, T., et al., Clin. Chim. Acta, 138:125–132 (1984).
Guilbault, G. G., Fluorescence Techniques in Cell Biology, pp. 235–242 (1973).
Undenfriend, S., et al., Fluorescence Assay in Medicine, II:412–429 (1969).
Undenfriend, S., et al., Fluorescence Assay in Medicine, II:321–323 (1969).

CBT

ABT

BBT

CBTP

ABTP

BBTP

FLUORESCENT BENZOTHIAZOLE DERIVATIVES

This application is a continuation of application Ser. No. 07/999,183, filed Dec. 28, 1992, now abandoned, which is a continuation of application Ser. No. 07/216,896, filed Jul. 8, 1988, now abandoned.

FIELD OF THE INVENTION

This invention relates to the field of fluorescent substrates, and also relates to the field of biological assays.

BACKGROUND

Measurement of the conditions or the presence of substances in an environment by detection of the rate of hydrolysis of an agent is well known. Specifically, the use of fluorescent substrates for such measurements is known, although such use is typically not practicable for measurements of very low levels of hydrolyzing agents, such as enzymes. Generally, by removal of a chemical moiety, the fluorescence of the compound increases. The prior compounds have been unsuitable, however, for measurement of low levels of enzyme in an aqueous environment.

All references herein cited are herein incorporated by reference.

A. Enzyme Measurement

Generally, the measurement of alkaline phosphatase (AP) has been used in diagnosis of various diseases because of its ubiquitous presence in the cell membranes of tissues in the body. Fernley, N. H., Mammilian Alkaline Phosphatases, in: Boyer, P. D. (ed.), The Enzymes, Vol. IV, Academic Press, New York 1971, pp. 417–447. Various esterases are also measured for clinical diagnoses of disease. Bergmeyer, H. U., Methods of Enzymatic Analysis, 3d.ed., Vol. IV, 1–143, Verlag Chemie, 1984. With recent advances in biological techniques, these enzymes could be used as markers in combination with biological probes for the detection of complementary biological molecules. Thus, the activity of the enzyme indirectly measures the quantity of the biological substance complementary to the probe. While various esterases may be used, alkaline phosphatase measurement provides a convenient assay for the detection and measurement of complementary biological molecules. Bergmeyer, supra, at Vols, 10–11.

Previously, the level of AP has been monitored using UV visible spectrophotometry, radioimmunoassay (RIA), and fluorescent substrates.

UV compounds have been tried for assays of AP, for example thymolphthalein monophosphate, Coleman, C. M., Clin. Chim. Acta, 13:401 (1966), phenolphthalein monophosphate, Wilkerson, J. H. and Vodden, A. V., Clin. Chem., 12:701 (1966) and para-nitro-phenylphosphate, Neuman, H. and Van Vrudendaal, M., Clin. Chim. Acta, 17:183 (1967). These compounds are approximately a thousand times less sensitive than efficient fluorescent compounds necessary to determine 10 attomole/mL ($10 \times 10^{-18}$ moles/mL) of AP.

There has been a variety of fluorescent substrates described in literature which have been used in assaying AP. None of these substrates have been entirely satisfactory for a variety of reasons.

7-Hydroxycoumarin phosphate, Glazer, R. and Haynes, M., Anal. Letters, 1 (5):333–45 (1968) and Sherman, William R. and Robine, Eli, Anal. Chem, 40/4:803–51 (1968), requires a high substrate level of 10 mM to saturate the enzyme. Its Stokes' shift is 78 nm (excitation of 376 nm and emission of 454 nm) and the Raman fluorescence of 422 nm. Since the Raman is close to the fluorescence maximum it can mask the signal being generated at 454 nm. Thus, these factors would have adverse effects on the ability of the substrate to measure very low levels of AP rapidly.

2-Benzoxazolyl-7-hydroxycoumarin phosphate, Wolfbeis, Otto S. and Koller, Ernst, Mikrochemica Acta, 389–95 (1985) has a low Stokes' shift of 44 nm (excitation of 427 nm with an emission of 471 nm). A second negative associated with this substrate is its low aqueous solution stability in tris pH 9.5 even at $-15°$ C.

2-Phenyl-7-hydroxycoumarin phosphate, Otto S. and Koller, Ernst, Mikrochemica Acta, 389–95 (1985) has a higher Stokes' shift of 88 nm (excitation of 383 nm with an emission of 471 nm), however it has poor aqueous solution stability, as noted for the previous compound.

Fluorescein phosphate has a Stokes' shift of 25 nm (excitation of 490 nm and emission of 515 nm). This small Stokes' shift makes it completely unsuitable for the determination of AP at low levels. See, Tiffany, T. O.; Watsky, M. B.; Burtis, C.a. and Thacker, L. H., Clin. Chem., 19/8:871–82 (1973).

3-Hydroxy-2-naphthanilide-6-bromo, 3-hydroxy-2-naphthyl-o-anisidine phosphate, Guilbault, G. G., Newer Fluorometric Methods for the Analysis of Biologically Important Compounds, In: Fluorescence Techniques in Cell Biology, Thaer, A. A. and Sernetz, M., ed., Springer-Verlag, N. Y., Heidelberg, Berlin, 235–42 (1983); Vaughn, A.; Guilbault, G. and Hackney, D., Anal. Chem., 43/6:721–4 (1971) and Guilbault, G. G., J. Res. NBA, 76A/6:607–12 (1972), has a Stokes' shift of 110 nm (excitation of 405 nm and emission of 515 nm). However, the 1971 reference noted that there is a residual fluorescence at 515 nm due to the remaining phosphorylated substrate which would reduce the ultimate sensitivity of the substrate. Also, this substrate has only been used in a solid surface assay in intact cells for microscopic visualization of the presence of AP. Because of the structure of this substrate it is likely that the hydrolyzed product would be insoluble under the basic aqueous conditions of assays of biological material. This would limit the usefulness of the substrate.

2-Hydroxy-3-naphthoic anilide phosphate, Tsou, K. C. and Matsukawa, Sadao, J. Med. Chem., 11/15:1097–9 (1968) has a Stokes' shift of 220 nm (excitation of 300 nm and emission of 520 nm). However this substrate has only been used in a histochemical assay system. The hydrolyzed product, 2-hydroxy-3-naphthoic acid anilide, has a low solubility which could complicate its use in a kinetic or end point assay. Also, its background fluorescence is reported to be relatively high, at 520 nm indicating its ultimate sensitivity might be low due to the high background reading.

3-0-Methylfluorescein phosphate (3-0-MFP), Hill, Hoyle D., Summer, George K., and Waters, Michael D., Anal. Biochem., 24:9–17 (1968); Wolfbeis, Otto S. and Koller, Ernst, Mikrochemica Acta, 389–95 (1985); Hashimoto, Shinya, Kobayashi, Kensei; Fujiwara, Kitao, Harabuchi, Hiroki and Fuwa, Keiichiro, Bunseki Kagaku, 32:E177–E184 (183) and Norgaard, Aage, Kjeldsen, Keld, Larsen, Jim Stenfatt; Larsen, Christian Gronhoj and Larsen, Frederik Gronhoj, Scand. Clin. Lab. Invest., 45/2:139–44 (1985) has a Stokes' shift of 15 nm. Hashimoto, et al., have also noted problems of hydrolysis of the phosphate under aqueous conditions suitable for the assay of AP.

Riboflavin-5-phosphate, Glazer, R. and Haynes, M., Anal. Letters, 1(5):333–45 (1968) and Takeuchi, T. and Nogami, S., Acta Pathol. Japan, 4, 277 (1954) has been used in tissue AP assays, only. The ultimate sensitivity of the assay has not been reported.

Flavone disphosphate has an emission wavelength of 510 nm. Glazer, R. and Haynes, M. Anal. Letters, 1 (5):33–45 (1968) and Land, D. B. and Jackim, E. Anal. Biochem., 16:481 (1966). The excitation wavelength was not reported. The authors reported that it was a more stable substrate than 3-0-MFP and a more sensitive fluorescence indicator than beta-naphthol phosphate. This substance requires the removal of two phosphate groups before the initiation of fluorescence can be observed. This would cause severe problems for a kinetic assay in which only a fraction of the starting substrate is converted to monophosphate which is not fluorescent. Then the monophosphate would have to be converted to the 3-hydroxy-flavone before the fluorescence emission could be observed.

4-methyl umbelliferyl phosphate (4-MUP), Wolfbeis, Otto S. and Koller, Ernst, Microchemical Acta, 389–95 (1985); Cornish, Coralie J., Neale, Francis C. and Posen, Solomon, Amer. J. Clin. Pathol., 53/1:68–76 (1970) and Sherman, William R. and Robine, Eli, Anal. Chem., 40/4:803–5 (1978), has a Stokes' shift of 82 nm with an excitation at 367 nm. Emission is 449 nm. The first order Raman is 416 nm which is 1/120 that of 4-methyl-umbelliferone (4-MU). The emission contributes to a high background fluorescence. Cornish et al. report that 4-MUP has an emission at 465 nm, which is 1/120 that of 4-methyl-umbelliferone (4-MU). It was also noted by these authors that the 4-MUP breaks down in basic tris buffer. They were able to decrease this hydrolysis problem by preparing the 4-MUP in a bicarbonate/carbonate buffer. Hashimoto, Shinya, Kobayashi, Kensei, Fujiwara, Kitao, Harabuchi, Hiroki and Fuwa, Keiichiro, Bunseki Kagaku, 32:E177–E184 (1983) reported that their survey of the literature showed that 4-MUP "seems the most promising substrate for further investigation on the dissolved enzymes (AP) in natural waters. Using this substrate with 48 hours incubation, the lowest limit of the determination of AP activity was $1 \times 10^{-12}$ moles $1^{-1}$ min$^{-1}$. On the other hand, that of conventional spectrophotometric method using p-NPP was $0.4 \times 10^{-9}$ moles $1^{-1}$ min$^{-1}$."

DeLuca, Marlene and McElroy, W. D., Meth. Anal. Chem., 40/4:803–5 (1968) report that L-(+)-luciferin (LH) in an aqueous pH 9.0 solution is a highly fluorescent compound with an excitation level of 385 nm, and with emission at approximately 540 nm. In an aqueous solution the quantum yield is 0.62. LH is an unstable compound in basic aqueous solutions.

2-carbamyl-6-methoxybenzothiazole, an intermediate in the synthesis of LH, is reported in Methods of Enzymology, Vol. 57, p. 19. There was no fluorescence reported for this material and this was verified in our experiments.

B. Environmental Condition Measurement.

Because environmental factors are known to cause hydrolysis of phosphate groups, monitoring of the rate of hydrolysis may indirectly monitor various environmental conditions. For example, extremes in temperature or pH, or metals may act as hydrolyzing forces. Accordingly, it is of value to have a fluorescent compound which is inhibited by attachment of a chemical moiety and which, upon cleavage of the chemical moiety by hydrolyzing forces, exhibits restored fluorescence.

The use of colorimetric tests for the presence of oxygen is known in the art, e.g., colorimetric tests for anaerobic environments. Fluorescent compounds may also be used for the measurement of oxygen level. Generally, where fluorescent compounds possess characteristic "long lifetime", the compound is capable of being quenched by the presence of oxygen. This occurs as electrons in the fluorescent compound drop down to a lower energy level as they emit light energy. If the time period in which the electrons drop is sufficient, some of the energy given off by the falling electron is harnessed by oxygen molecules. The minimum "lifetime" for the falling electron is approximately $10^{-15}$ seconds, but a longer lifetime provides for a more sensitive oxygen measurement. Accordingly, it is of value to have a fluorescent compound with "long lifetime" in order to measure oxidation.

C. Direct Detection, Assaying or Monitoring of Biological Molecules.

Labels for biological ligands are well known in the art, and these include radioactive substances, colorimetric indicators and fluorescent compounds. Typically, these substances are either incorporated into the biological ligand, as in the use of radioactive nucleotides, or are chemically attached to the ligand, as in the use of glutaraldehyde or various chemical "extension arms" which are used to attach fluorescent labels to antibodies.

Accordingly, the present invention provides the following advantages:

1. Fluorescent compounds which maintain stability in an aqueous environment;
2. Fluorescent compounds which are easily detectable above background interference;
3. Fluorescent compounds, which, upon attachment of a chemical moiety, severely decrease in fluorescence but, upon removal of said chemical moiety, are strongly fluorescent;
4. Fluorescent compounds which exhibit a Stokes' shift sufficient for use as an assay indication or other marker; Fluorescent compounds which provide means for detection of at least about 10 attomolar ($10^{-18}$ molar) concentrations of alkaline phosphatase;
5. [sic]
6. Fluorescent compounds which possess "long lifetime" and provide means of detecting oxidizing agents;
7. Fluorescent compounds which maintain fluorescence characteristics in a variety of solvents;
8. Non-fluorescent phosphate compounds which are stable in water which can form fluorescent compounds upon hydrolysis;
9. A class of fluorescent compounds of which some members can be excited with visible light.

SUMMARY OF THE INVENTION

This invention relates to the use of derivatives of benzothiazole (BT) as fluorescent substrates. Highly fluorescent derivatives of BT can be converted to non-fluorescent derivatives by the attachment of a chemical moiety to the BT derivative. When the chemical moiety is cleaved or otherwise dissociated from the non-fluorescent derivative, the fluorescence is restored.

Previously, no simple benzothiazole derivatives were shown to be fluorescent. Although a few fluorescent benzothiazole compounds are reported in the literature, the actual fluorescence characteristic was neither reported nor known. 2-carbamyl-6-methoxybenzothiazole had previously been reported to be a non-fluorescent derivative of luciferin, see supra, and this has been confirmed in our hands. Both 2-cyano-6-hydroxybenzothiazole (CBT), Deluca, M. A. and McElroy, W. D., Methods of Enzymology, 57:15–24 (Academic Press), and 2-carbamoyl-6-hydroxybenzothiazole, Faure, R. et al., Org. Magn. Reson. 11:617–27 (1978), are reported in the literature, but neither the fluorescence of such compounds, nor the inhibition of fluorescence of such compounds by an attached chemical moiety, is reported. There was no indication that benzothiazole derivatives may be fluorescent, under what conditions such fluorescence is exhibited and under what conditions fluorescence is inhibited. Thus, the fluorescent properties of CBT, as well as ABT and other BT derivatives are unexpected in view of the reports of these compounds prior to the present invention.

This invention also relates to the use of the fluorescent derivatives of BT without an attached chemical moiety. These compounds can be used to directly assay biological molecules, as, for example, by labelling biological molecules.

Derivatives of BT can also be used to measure oxygen levels. As the oxygen appropriates the energy emitted by the excited electrons dropping to lower energy states in the fluorescent derivatives of BT, the fluorescence of fluorescent derivatives of BT molecule decreases. Thus the decrease in the fluorescence indicates the amount of oxygen present in the assay system.

Another aspect of the present invention is the ability of the fluorescent derivatives of BT to maintain fluorescence in organic solvents. Thus, use in both water and organic solvents for the detection and measurement of conditions and substances in an environment, is possible.

The class of fluorescent compounds described herein is comprised of those compounds represented by the diagram:

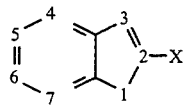

wherein:
a) At least one of the carbons of positions 4, 5, 6 or 7 is linked to a chemical moiety containing an anion group which is attached to the benzene ring; and;
b) The carbon at position 2 is linked to a chemical moiety comprised of at least two atoms which extend resonance of the benzothiazole ring system; and,
c) A nitrogen atom is located at position 3; and
d) A sulfur atom is located at position 1.

An anion group in resonance with the benzene ring, for example, an ionizable hydrogen, is necessary for the addition of a chemical moiety suitable for inhibition of fluorescence. The dual-atom chemical moiety linked to the 2-carbon is a necessary extension of the resonance system for fluorescence. It has been herein discovered that with increasing length and conjugation of the chemical moiety linked to the 2-carbon, the wavelength of light emitted from the compound and the excitation wavelength is also increased. Thus, by increasing the number of atoms in the chemical moiety attached to the 2-carbon, the fluorescence will appear deeper in hue.

Herein, the following terminology is used as defined below:
ABT: 2-carbamoyl-6-hydroxybenzothiazole
BBT: 2'-(2-benzothiazolyl)-6'-hydroxybenzothiazole
CBT: 2-cyano-6-hydroxybenzothiazole
Stokes' shift: a physical constant that is characteristic of luminescent molecules which is the difference between the wavelength of the excitation and emission maxima.
Rayleigh-Scatter: interference due to light emitted as a result of electron vibration due to excitation by photon energy.
Raman: appears in fluorescence spectra at higher and lower wavelengths than the Rayleigh-scatter peak. These Raman bands are satellites of the Rayleigh-scatter peak with a constant frequency difference from the exciting radiation. These bands are due to vibrational energy being added to, or subtracted from, this excitation photon.
Fluorescence efficiency: the amount of light emitted as a proportion of that used to excite.
Excitation wavelength: the wavelength of light used to generate fluorescence emission, measured in arbitrary units.
Emission wavelength: the wavelength of light emitted by a fluorescent molecule after excitation.
Km: the substrate concentration at which the velocity of the enzymatic reaction is half maximal.
Turnover number: the number of substrate molecules transformed per unit time by a single enzyme molecule when the enzyme is the rate limiting factor.
Molar absorptivity: the intensity of an absorption band in the ultraviolet or visible spectrum.
Substrate: the molecule on which the enzyme exerts a catalytic action.
Enzyme: catalyst capable of greatly enhancing the rate of specific chemical reactions.
Resonance: when the contribution of each of several structures is to be weighted in some way that accords with the degree of bonding each would have if it represented an actual molecule with the specified geometry.

DETAILED DESCRIPTION OF THE INVENTION

The following description provides details of the manner in which the embodiments of the present invention may be made and used in order to detect and measure very low levels of enzyme or other hydrolyzing agents using a fluorescent substrate. This description, while exemplary of the present invention, is not to be construed as specifically limiting the invention. Such variations which would be within the purview of one skilled in this art are to be considered to fall within the scope of this invention.

Figure 1:
FIG. 1 represents the structure of CBT, ABT and BBT.
Figure 1:
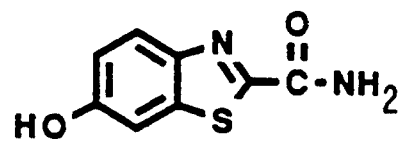
Figure 1:
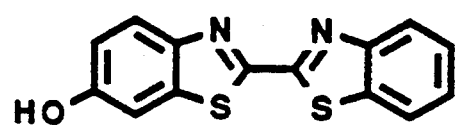

Specifically, the compounds 2-cyano-6-hydroxybenzothiazole (CBT), 2-carbamoyl-6-hydroxybenzothiazole (ABT), 2'-(2-benzothiazolyl)-6'-hydroxybenzothiazole (BBT), are fluorescent in a basic aqueous solution from 445 nm–580 nm (ABT and CBT), and 460 nm–660 nm (BBT) with the maximum for the emission occurring at 510 nm, 518 nm and 561 nm respectively. The excitation occurs over a range from 320 nm–430 nm (CBT), 325–440 nm (ABT), and 330 nm–480 nm (BBT) with the maximum occurring at 381 nm, 381 nm, and 419 nm respectively. See FIG. 1 for the structures of these compounds, and Table 1 for a summary of the above data.

Figure 2:
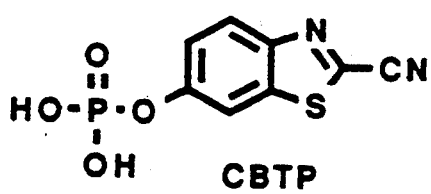
FIG. 2 represents the structure of CBTP, ABTP and BBTP.
Figure 2:
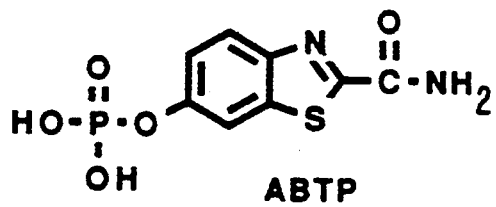
Figure 2:
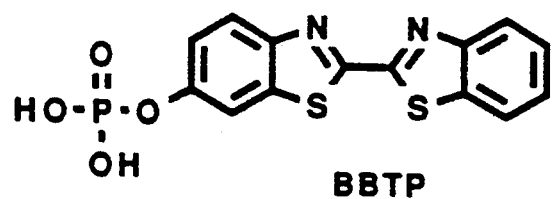
Figure 3:
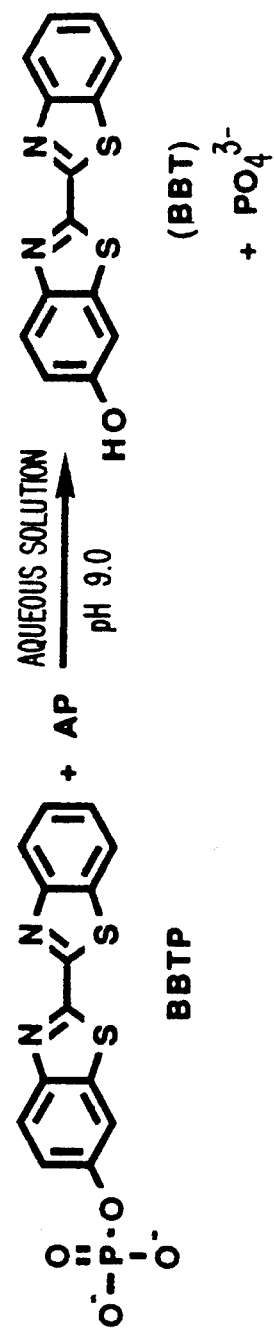
FIG. 3 is a diagram illustrating one way in which BBTP is used to measure alkaline phosphatase (AP).

A chemical moiety may be added to the fluorescent derivatives of hydroxybenzothiazole which severely inhibits the fluorescent capabilities of the molecule. When the attachment of the chemical moiety provides a suitable substrate for an enzyme, the moiety is cleaved from the non-fluorescent derivative of hydroxybenzothiazole molecule, and the fluorescence is restored. In this way, for example, CBT, ABT and BBT, can be used as a fluorescent marker for the detection of enzymatic activity. A phosphate moiety, for example, may be added to BBT to produce the non-fluorescent derivative 2'(2-benzothiazole)-6-hydroxybenzothiazole phosphate (BBTP), a suitable substrate for alkaline phosphatase. Upon cleavage of the phosphate moiety by alkaline phosphatase (AP), the fluorescence provides, therefore, measurement of the enzyme activity. The enzymatic reaction of AP with BBTP is shown in FIG. 3. The molecular structure of phosphate derivatives prepared are shown in FIG. 2.

Other chemical moieties may be attached to BBT. Examples include chemical moieties providing for a sufficient substrate for choline esterase, cholesterol esterase, lipases, and any moiety which is capable of being cleaved from the non-fluorescent derivative of hydroxybenzothiazole by an enzyme. Moieties capable of being cleaved by other hydrolyzing forces may also be attached for purposes of assaying these hydrolyzing forces.

Figure 4:
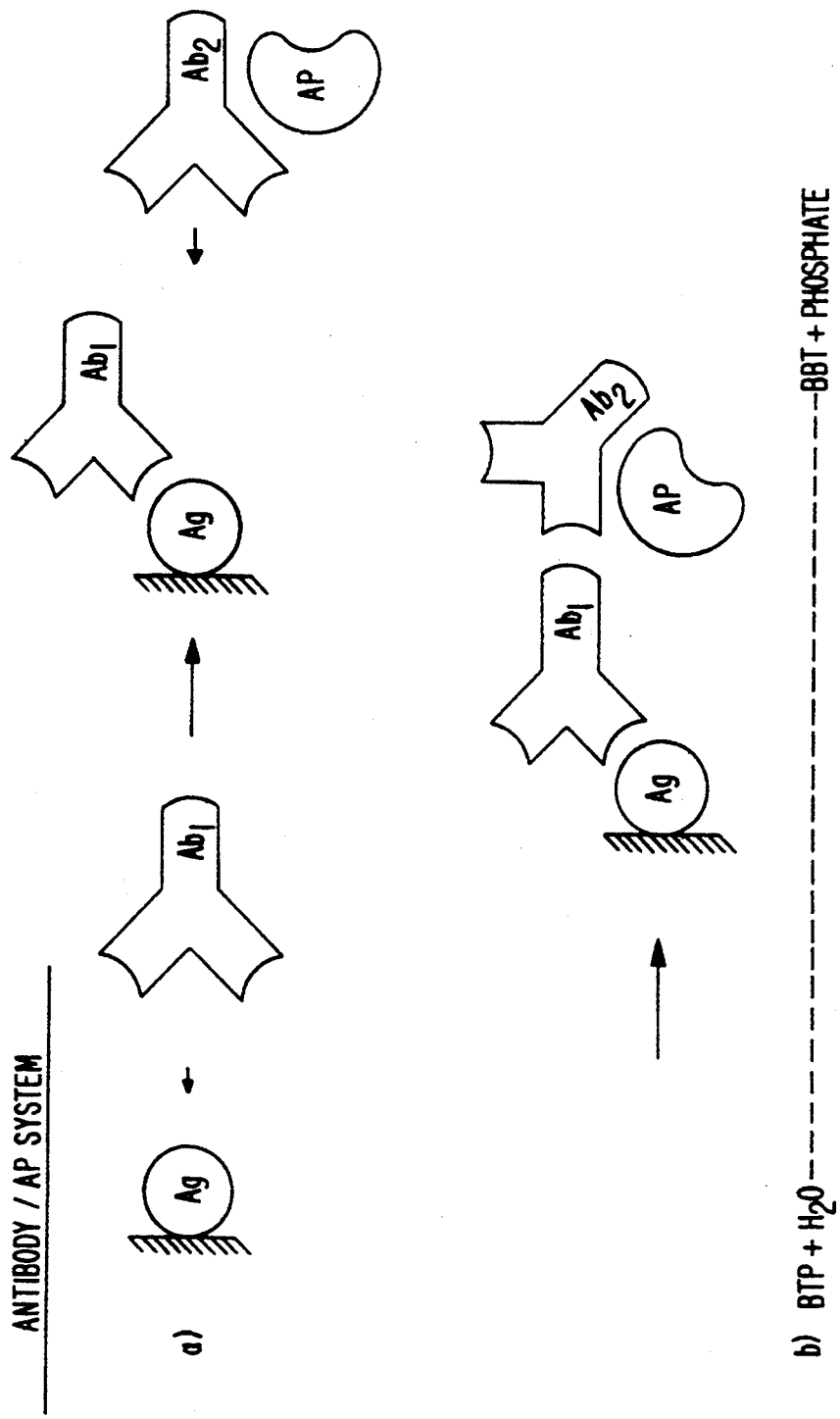
FIG. 4 shows one way in which BBTP is used to measure material complementary to an antibody upon which alkaline phosphatase (AP) is attached. The antibody/AP complex is bound to a complimentary molecule. The AP acts to cleave the phosphate moiety from phosphorylated BBT and thereby restore fluorescence. The measurement of the fluorescence thus indicates the presence and quantity of the-complementary molecule.

In addition, CBT, ABT, and BBT may be used indirectly or directly for an assay of biological molecules. The enzyme may be bonded to biological ligands, such as monoclonal or polyclonal antibodies or fragments thereof, nucleic acid probes or other biological compositions capable of detecting a complementary molecule. In this way, the enzyme/ligand first binds to a complementary biological molecule, and, with the addition of a substrate comprised of CBT, ABT or BBT with a suitable chemical moiety under suitable conditions, the enzyme cleaves the chemical moiety and the CBT, ABT or BBT exhibit strong fluorescence. Detection or measurement of this fluorescence enables the detection and measurement of the biological material complementary to the probe. Note that such assays can be performed using biological sample such as urine, blood, or tissue sample. An example of using a phosphorylated CBT composition and alkaline phosphatase is shown in FIG. 4. Direct measurement of biological molecules can be accomplished by attaching ABT, BBT or CBT to a biological ligand via methods known to those skilled in the art, and detecting the fluorescent signal.

Another aspect of the present invention is the use of CBT, ABT or BBT to measure free radicals, such as oxygen concentration, particularly in blood. Because free radicals such as oxygen can appropriate the energy emitted during fluorescence, decreasing fluorescence of derivatives may be correlated to oxygen content. Thus, measurement of fluorescence can be used to detect oxygen concentration.

It should be noted that because CBT, ABT and BBT maintain fluorescence characteristics in different solvents, the compound may be used to perform such measurements in different solvents. See, Table 3.

DESCRIPTION OF THE PREFERRED EMBODIMENTS

1. Equipment Used

The UV/VIS instrument was a Beckman model number 25. The NMR instrument was a Varian model EM3-60A 60 mHz proton unit or on General Electric GN-500 500 Mg hertz unit. The NMR shifts are reported using tetramethylsilane as the internal standard. One fluorometer was a Spsex II Fluorolog model 112 with a single monochromator for excitation and a double monochromator for emission. It was run using front face fluorescence. The second fluorometer was a Turner model 111 with filters purchased from Turner. The melting points are uncorrected and were determined on Thomas Hoover capillary melting point instrument. The HPLC instrument was a Waters dual pump (model M-6000) unit equipped with a solvent programmer (model 660) and a UV/VIS fixed wavelength detector (model 440). The column used was a 3.9×25 mm Waters reverse phase C-18 10 micron irregular silica gel Solution A used for the HPLC analysis was prepared using 3000 mLs of HPLC grade water and 750 mLs of HPLC grade methanol with 5.52 g of monosodium phosphate monohydrate. Unless otherwise specified the flow used for the HPLC analysis was 1.0mL per minute. The reactor vials used were 1 mL to 10mL size made of pyrex glass which had a silicone septum with teflon face on the reagent side and an internal teflon magnetic stirring bar. The pH was determined using a Fisher Accumet digital model 520. Before any equipment was used which came in contact with the substrate solutions it was soaked in 1N hydrochloric acid for three hours and then rinsed thoroughly with freshly distilled deionized water. This usually ensured that the ambient AP present was destroyed. Each individual lot of bovine serum albumin used from Sigma was evaluated for level of AP present.

2. Reagents Used

The reagents and solvents used, unless otherwise specified, were ACS reagent grade. The DEA used was vacuum distilled in glass before use. The tetrahydrofuran (THF) used was dried over calcium hydride and distilled immediately before use. The water used was freshly deionized (2 megaohm) and distilled. The AMPD was supplied by JBL Scientific catalog number 1250A. Triethylamine, benzothiazole and 2-amino-thiophenol were obtained from Aldrich. Trimethyl bromosilane was obtained from Petrarch Systems. The 2-chloro-6-hydroxybenzothiazole, 2-amino-6-hydroxybenzothiazole and 2-cyano-6-methoxybenzothiazole were kindly provided by professor Neil Baggett, Department of Clinical Chemistry of the University of Birmingham, Birmingham, United Kingdom. These compounds were prepared using the procedures described by Bowie, L. J. (1978) Methods in Enzymology (Deluca, M. A., ed.), Vol. 57, pp. 15–28, Academic Press, N.Y.

3. Fluorescence Properties a. Fluorescence Properties of CBT, ABT and BBT

The fluorescence properties of CBT, ABT, and BBT benzothiazole (BT), 2-chloro-6-hydroxybenzothiazole (Cl-BT), 2-amino-6-hydroxybenzothiazole (Amino-BT), and 2-cyano-6-methoxybenzothiazole (CN-Methoxy-BT) were measured in aqueous pH 10.2 solution with 0.1M 2-amino-2-methyl-1,3-propanediol (AMPD). The approximate fluorescence efficiency was determined by dissolving the appropriate compound in a suitable solvent (methanol or ethanol) giving 10mg per 10 mLs of solvent. Then 100 microliters of this solution was added to 9.9 mL buffer containing 0.1M 2-amino-2-methyl-1,3-propanediol (AMPD) pH 10.0. A hand held fluorescence source (254 nm) was used to excite the solution in a quartz cell and visual observations were recorded. If this solution was fluorescent it was diluted 1/10 and the measurement repeated. It was found that BT, Cl-BT, Amino-BT and CN-Methoxy-BT are all at least three orders of magnitude lower in their fluorescent efficiency than CBT, ABT, and BBT. Thus it appears that when the benzothiazole moiety contains an ionizable group in the benzene ring, and a group in the two position which extends the conjugation, fluorescence capabilities can be dramatically increased.

The fluorescence properties of CBT, ABT and BBT were measured and compared to those of 4-methylumbelliferone (4-MU). This information is presented in Table 1. See, Wolfbeis, Otto S. and Koller, Ernst, Mikrochemica Acta, 389–95. First the molar absorptivity (Emax) of CBT, ABT, and BBT was 15,500, (aqueous 0.10M AMPD pH 10.2) 13,300, (aqueous 0.392M sodium carbonate pH 11.0) and 33,000 (aqueous 0.1M DEA pH 10.0). These molar absorptivities were measured at 378 nm, 368 nm, and 415 nm respectively. Secondly, the excitation maximum were found to be 381 nm for both CBT and ABT with BBT having its excitation maximum at 419 nm. The emission maximum was found at 510 nm, 518 nm, and 561 nm for CBT, ABT, and BBT respectively. The Stokes' shifts were 129 nm, 137 nm, and 142 nm respectively. These data were collected using Spsex II front face fluorescence in 0.10M AMPD, pH 10.0. The Raman for water was found at 433 nm for CBT. Thus the Raman for water will not interfere with the assay. These data clearly show that these compounds had the desirable Stokes' shift and the water Raman was well removed from the fluorescence emission.

Figure 11:
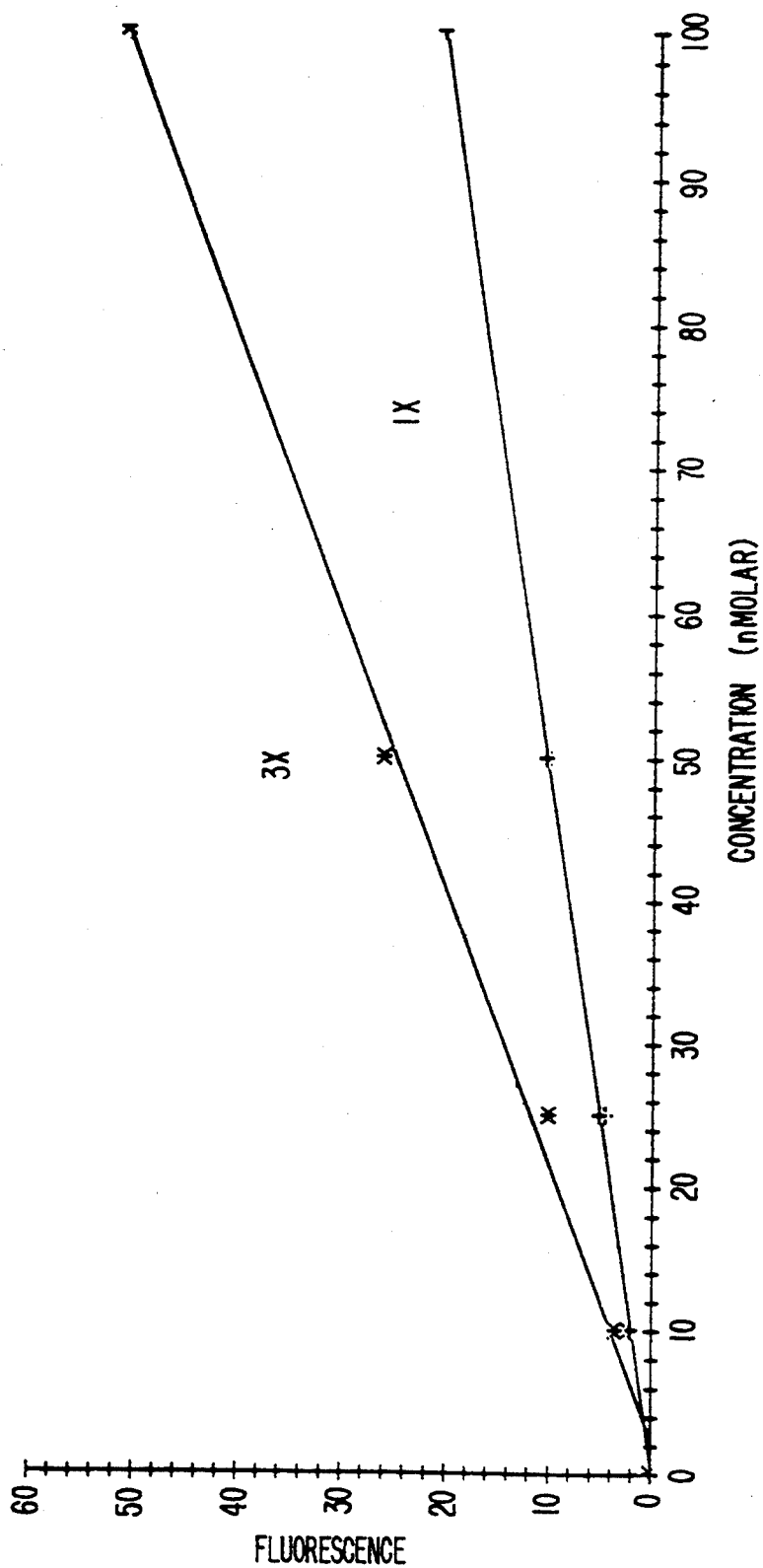
FIG. 11 is a graph showing the fluorescence of ABT versus concentration.
Figure 12:
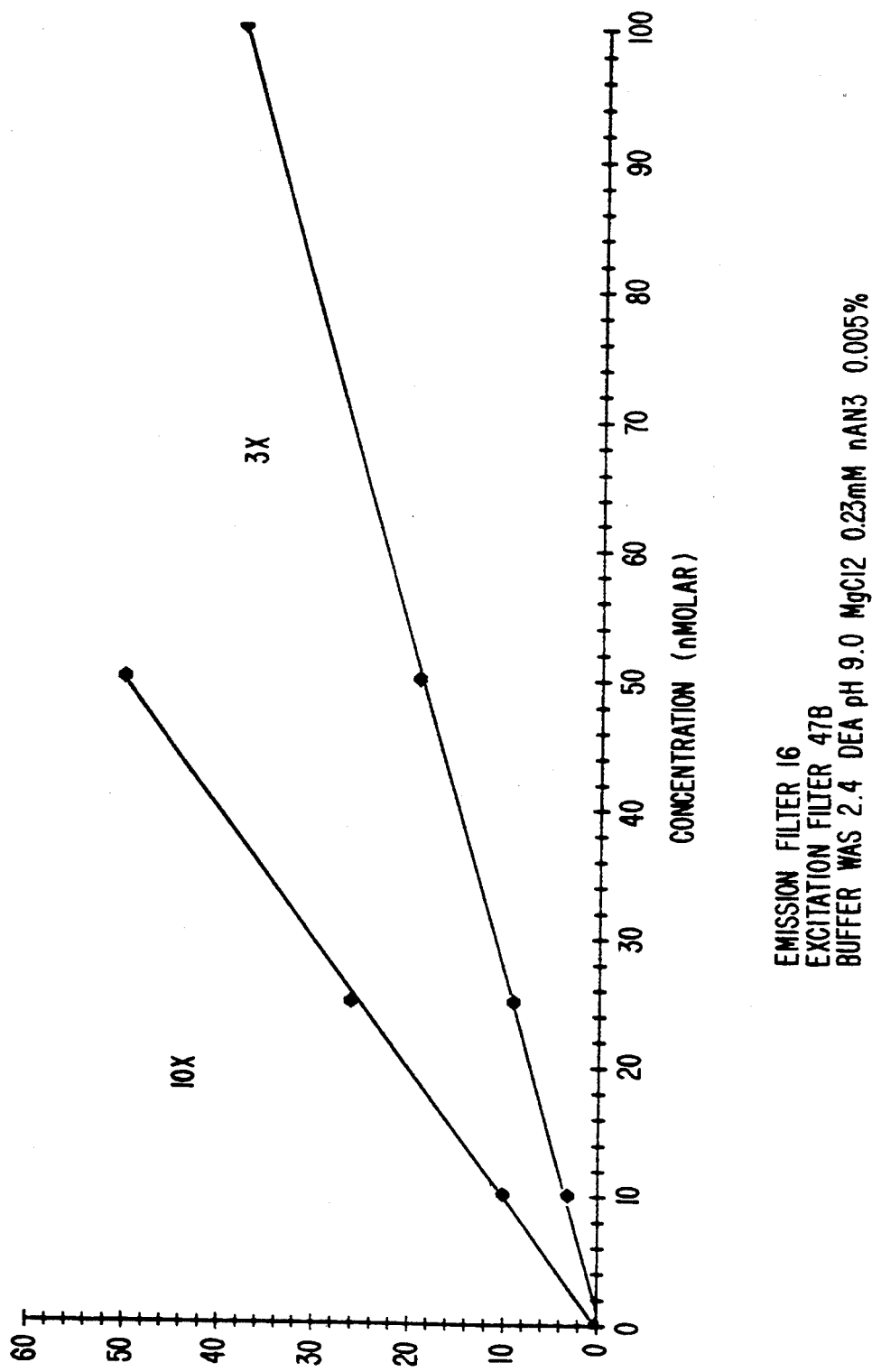
FIG. 12 is a graph showing the fluorescence of BBT versus concentration.

The next factor to be determined was the fluorescence efficiency. Typically, a fluorescence efficiency of approximately 1% is considered practicable, and 4-MU has characteristic 20–40% efficiency. A comparison was made between CBT and 4-MU. Each compound was excited at its excitation maximum. Using front face fluorescence it was found that 4-MU gave 6.86 counts/femtomole and the CBT under identical conditions, gave 2.85 counts/fm. Thus the CBT was very close to the fluorescence efficiency of 4-MU. See FIGS. 11 and 12 for the fluorescence sensitivity of ABT and BBT. Fluorescence data were collected using a Turner model 111. The curves are linear at both 1 x and 3 x ranges over 10 to 100 nanomolar.

b. Fluorescence Properties of CBTP

CBT was phosphorylated to form CBTP 2-cyano-6-hydroxybenzothiazole phosphate (CBTP). The structure is shown at FIG. 2. Unexpectedly, CBTP exhibited very low levels of fluorescence, indicating that the phosphate moiety severely inhibits fluorescence of CBT.

The fluorescence data for CBTP was determined as follows. One mg of CBTP was dissolved in 2.0 mL of buffer: 0.10M AMPD, 0.10 m NaCl, 1.0 mM $MgCl_2$, 0.10 mM $ZnCl_2$, pH 10.2. This stock solution was diluted 10 microliters to 500 microliters in buffer. The settings were 700 volts on the high voltage side. The excitation maximum was 377 nm with maximum fluorescence of 53,000cps at 504 nm. A small quantity of AP was added to hydrolyze the CBTP to form CBT. After this was completed, the readings at 501 nm were off-scale. By reducing the high voltage to 500 volts, the excitation maximum was 378 nm, with a maximum fluorescence of 808,000cps at 501 nm. This reduction from 700 to 500 volts on the high voltage power supply reduces the sensitivity by approximately an order of magnitude. Thus, the CBTP has no measurable fluorescence when excited from 300 to 400 nm. The small fluorescence seen was probably due to low levels of CBT present as a contaminant in the CBTP. See, Table 2.

Moreover, CBTP displays no measurable emission at 505 nm, which was the emission wavelength for the expected hydrolyzed product, CBT. This confirms the low interference in the AP assay due to the emission of CBTP.

The next critical factors to be determined for CBTP were the approximate $K_m$ and the turnover number with AP. This determines how quickly and efficiently AP cleaves the phosphate moiety from CBT. The CBTP-di(AMPD) salt was compared directly to para-nitrophenylphosphate, di-tris salt (pNPP,di-tris) and 4-methyl umbelliferyl phosphate, di-(AMPD) salt. The UV/VIS assay was run in 0.1M AMPD, pH 10.2, 30° C. using 375 nm for CBT (15,500 Emax) and 405 nm for pNPP-di-tris (18,000 Emax) and 363 nm for 4-MU. The enzyme used was calf intestine AP, (Calzyme), 30,000u/mL, diluted 1/20,000 in AMPD buffer. The reference side contained 500 microliters of buffer as described. For example, the sample side contained 465 microliters of buffer, 25 microliters of substrate solution (stock solution being 20 mM substrate in AMPD buffer) and 10 microliters of the 1/20,000 diluted AP enzyme. It was found that CBTP had a turnover number which was 78% of the pNPP and 95% of the 4-MUP under identical conditions. Thus, CBTP has a high turnover number with AP. The maximum rate of CBTP turnover with AP under these conditions was at 2 mM. It was also found that ABTP and BBTP had a Km of approximately 2 mM under similar conditions. As within the skill of the art, these compounds may be used with a broad range of AP concentrations, which are typically practicable between about 0.05 mM and about 20 mM.

One key factor which limits the ultimate sensitivity of the fluorescence measurements in which an enzyme reacts with a substrate to form a fluorescent compound results from the interference from background fluorescence. This background is due to four factors: Raman fluorescence of the water, the Rayleigh scattering, tail fluorescence emission from the starting substrate, and fluorescence emission from free hydrolyzed substrate present in the substrate. To determine if the background fluorescence from contaminating hydrolyzed substrate was a problem, HPLC scans were run on both 4-MUP and CBTP to accurately determine the level of hydrolyzed substrate present in each. The CBTP had 0.08% CBT, and the 4-MUP contained 0.07% 4-MU (by weight). Since the levels of free hydrolyzed substrate were comparable and the fluorescence sensitivity was within a factor of 2.4 for 4-MU and CBT, as seen above, then any fluorescent background measured would be due to a combination of the first three factors described above. Using front face fluorescence, a 1 mM solution of 4-MUP gave an initial background reading of 297,640 cps (excitation, 366 nm; emission 444 nm). Using 1 mM CBTP (excitation, 391 nm; emission, 505 nm), the background reading was 42,518 counts/min. These readings were taken in 0.10M AMP, 0.1M NaCl, pH 10.2. Thus, it can be seen that the 4-MUP has a significantly higher background than the CBTP.

Next, the fluorescence of CBT was evaluated in different solvents in the presence or absence of base, cyclohexylamine (CA). These data are shown in Table 3.

The experiment was run by dissolving 5 mg CBT in 10 mL of dimethylsulfoxide. This solution (10 microliters) was added to 9.99 mLs of the appropriate solvent (Solution 1). This solution was transferred to a quartz UV cell and excited with a 254 nm hand held light source. The fluorescence was recorded after visual observations. Ten microliters of cyclohexylamine (CA) was added to solution #1 and the fluorescence recorded as above (Solution 2). Lastly, 100 microliters of CA was added to Solution 2 and the fluorescence recorded. Different solvents can thus be used and the characteristic green fluorescence will be observed that is seen when CBT is in an aqueous buffered basic solution.

A pH study of fluorescence was performed in aqueous solution with 0.10M sodium phosphate, pH 8.85 and 0.10M HCl. This study was carried out in an analogous manner to the process described above. The solutions displayed the characteristic bright green fluorescence until the pH was below 3. Between a pH of 3 and 1, an extremely acidic environment, the CBT solution lost its fluorescence. Thus it is clear that CBT maintains its fluorescence over a wide pH range.

It was found that CBTP will convert to ABTP in an aqueous basic environment. This conversion results in non-linear kinetics when CBTP is reacted with AP. Thus unless the reactions are carried out rapidly at 4° C. the CBTP converts to ABTP.

c. Fluorescence Properties of BBTP

Figure 5:
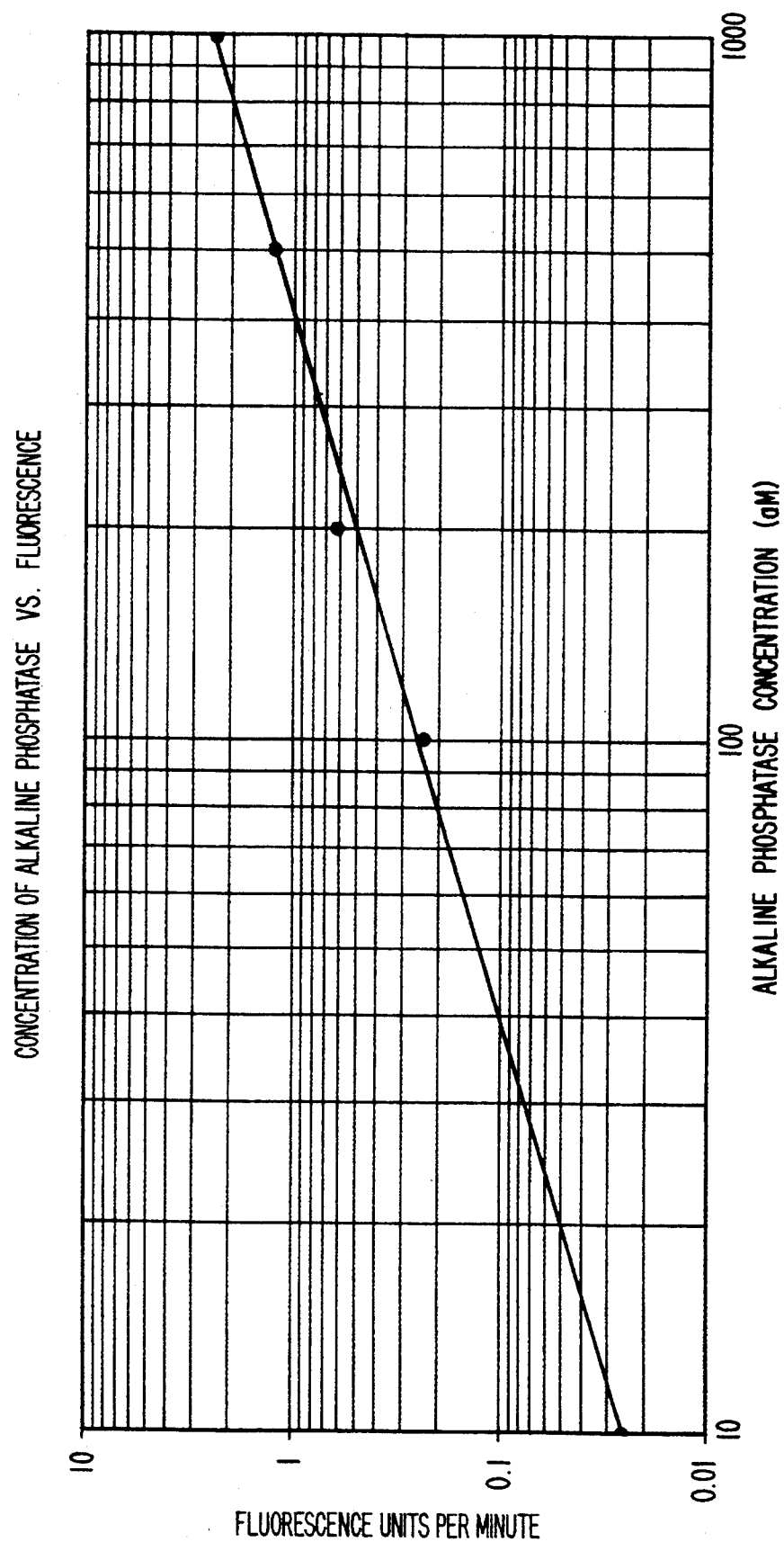
FIG. 5 is a graph showing the sensitivity of BBTP to AP. BBTP is shown to measure 0.3 attomoles of AP in a volume of 3.0 mLs. With a suitable instrument the cell volume could be reduced to 10 or 100 microliters, resulting in a projected sensitivity of 0.001 or 0.01 attomoles respectively. Note that a sensitivity of 0.001 attomoles represents 600 copies of AP determined in a 60 minute assay time.

The sensitivity of BBTP for detecting AP was next determined. See FIG. 5. The enzyme diluting buffer contained 0.10M diethanolamine, 1.0 mM magnesium chloride, 0.1 mM zinc chloride, 0.005% sodium azide at pH 9.0. The enzyme used was Calzyme, #27-5-24, 30,000 units/mg, containing 0.15 mM alkaline phosphate. Serial dilutions were performed to yield a 300 fM ($10^{-15}$M) (Solution E) and a 30 fm (Solution F) dilution. The substrate solution buffer contained 2.4M DEA, pH 9.0, 0.23 mM magnesium chloride, 0.005% sodium azide and 1.0 mM substrate. One through 10 microliters of either Solution E or F was added into 3.0 mLs of the substrate solution which was already equilibrated in the Turner Model 111 to a temperature of 35° C. The slope was measured using a strip chart recorder. The filters used for 4-MUP, CBTP and ABTP were the 760 on the excitation side and a 2A and 47B on the emission side. For BBTP the excitation filter was a 47B and the emission filter was a 16. These slopes were plotted against the concentration of the AP. FIG. 5 shows that using BBTP one can measure a 100 aM solution of AP in 30 minutes or a 10 aM solution in six hours. This system used as 3.0 mL reagent volume, however, if the reagent volume is reduced to 100 microliters then 6,000 copies or 0.01 attomoles of AP can be measured in 30 minutes or 600 copies or 0.001 attomoles in six hours.

d. Stability of BBTP and ABTP

Figure 6:
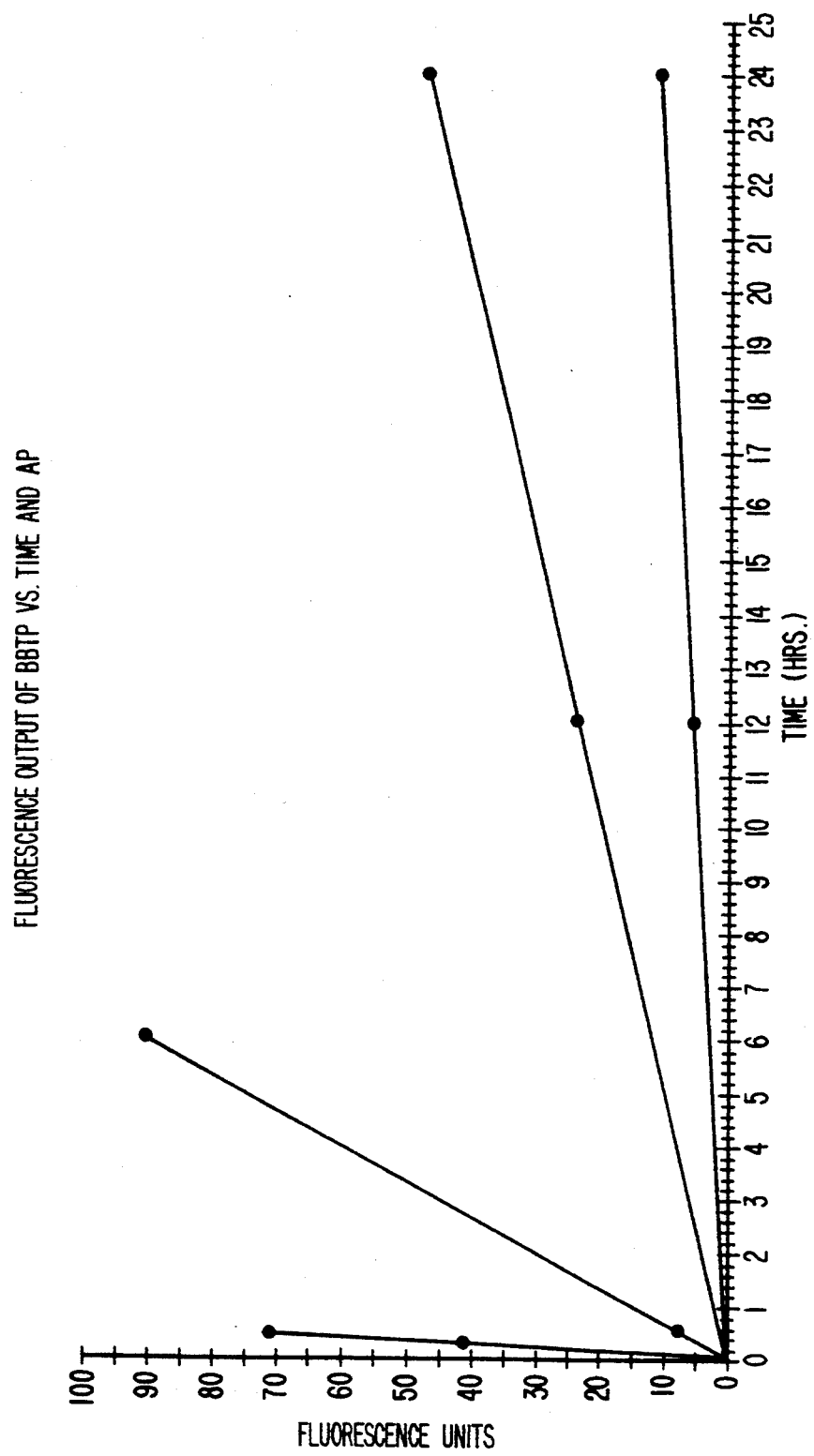
FIG. 6 is a graph showing the rate of hydrolysis of BBTP at 35° C. and the corresponding increase in the background fluorescence. Also, the rate of reaction of 10aM, 100aM and 1000 aM solutions of AP with BBTP are given.

The solution stability of BBTP in an aqueous solution of 2.4 mM DEA, pH 9.0, 0.23 mM magnesium chloride and 0.005% sodium azide was determined at 35° C. The results are given in FIG. 6, also shows the sensitivity of BBTP to 10 aM, 100 aM and 1000 aM AP. The data for the background fluorescence show BBTP to be a very stable substrate even in basic aqueous environment containing metals. It also shows the contribution of background to measurements of very low levels of AP, including the measurement of a 10 aM solution of AP over the background readings after at six hours.

Figure 7:
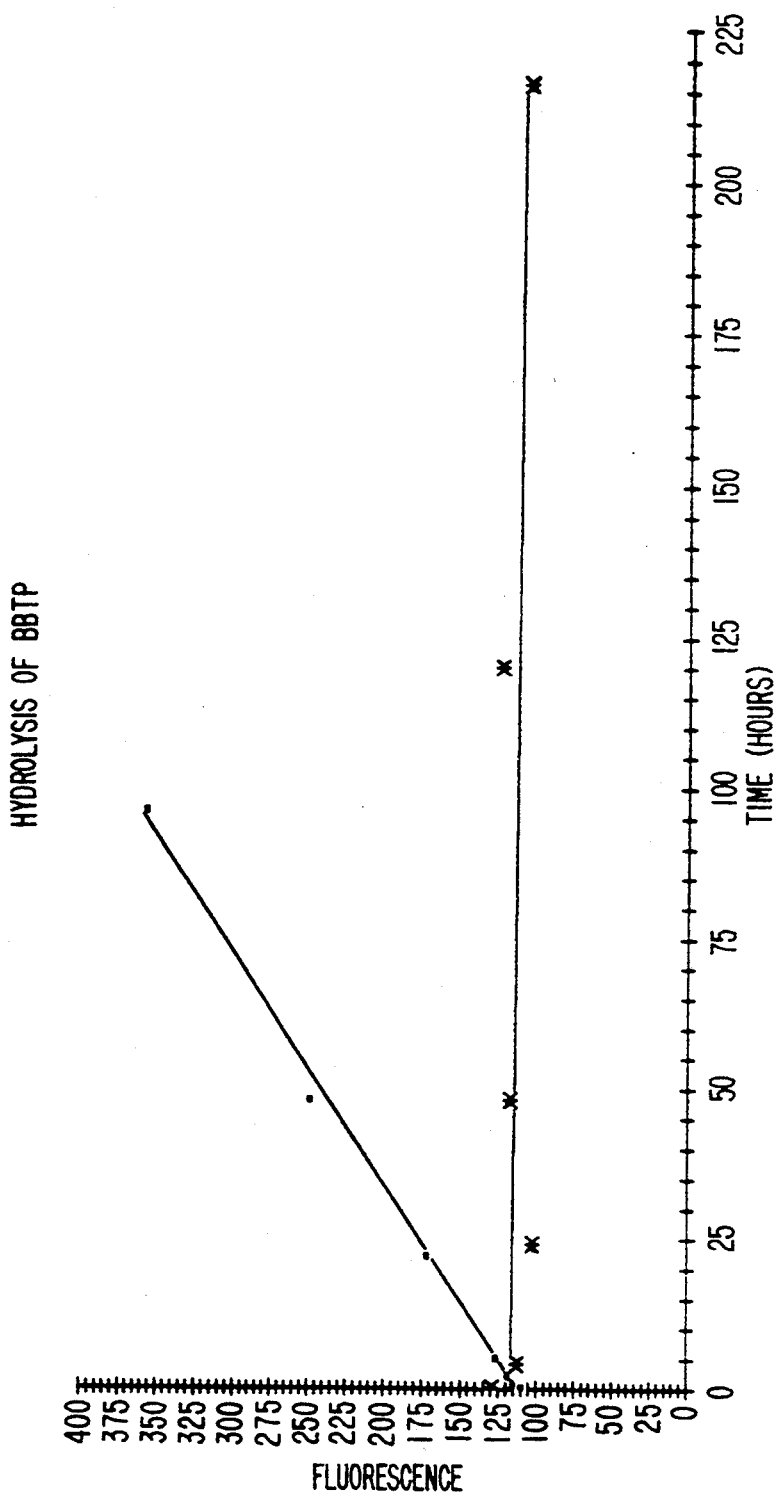
FIG. 7 is a graph of the background fluorescence of BBTP versus time in an aqueous solution at 4° C. and 35° C.
Figure 8:
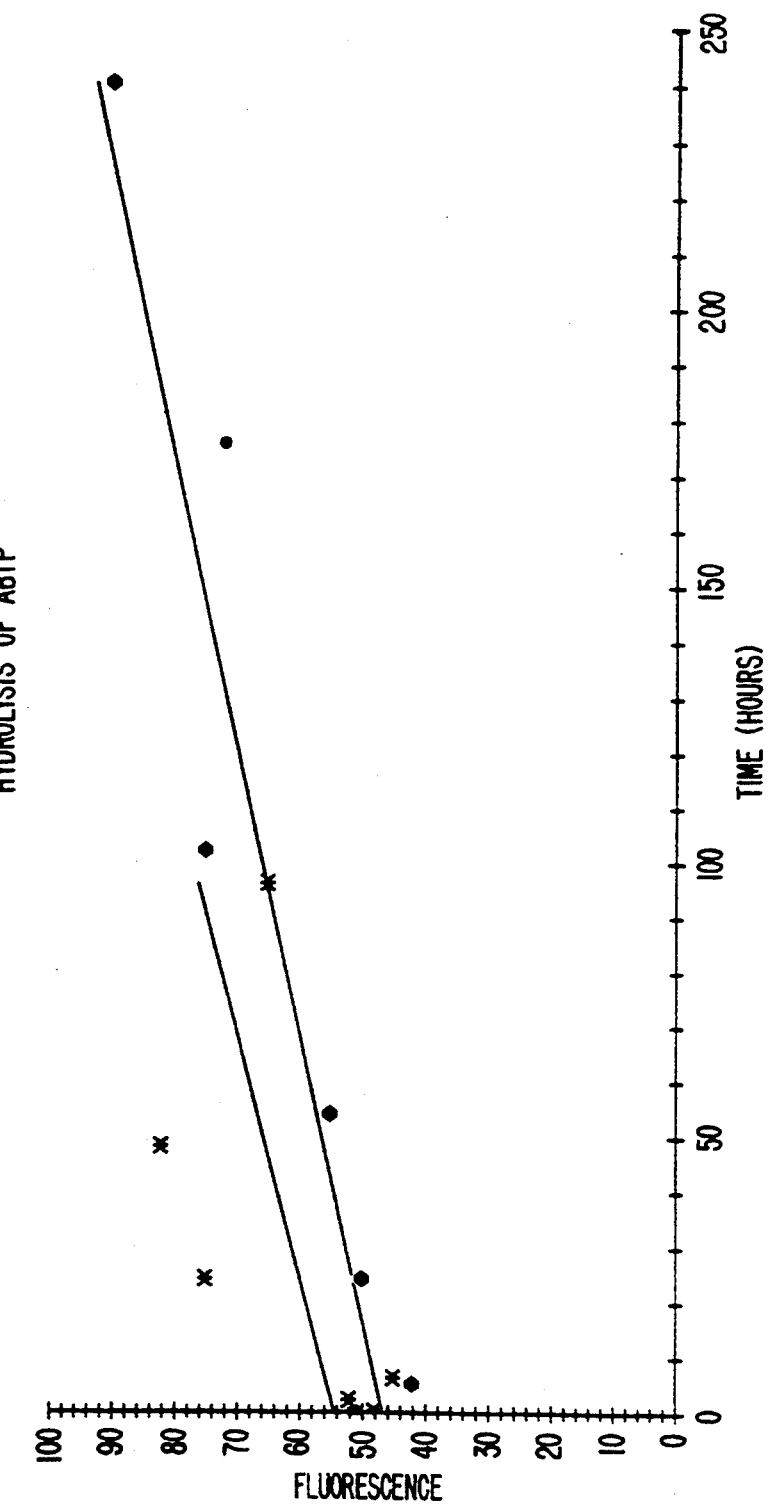
FIG. 8 is a graph of the background fluorescence of ABTP versus time in an aqueous solution at 4° C. and 35° C.

Along with this it was found that aqueous solutions of 1.0 mM BBTP could be prepared in the buffer described above and left at 4° C. ABTP stability at 4° C. was also measured. The results shown FIGS. 7 and 8 indicate stability of BBTP and ABTP at 4° C.

Figure 9:
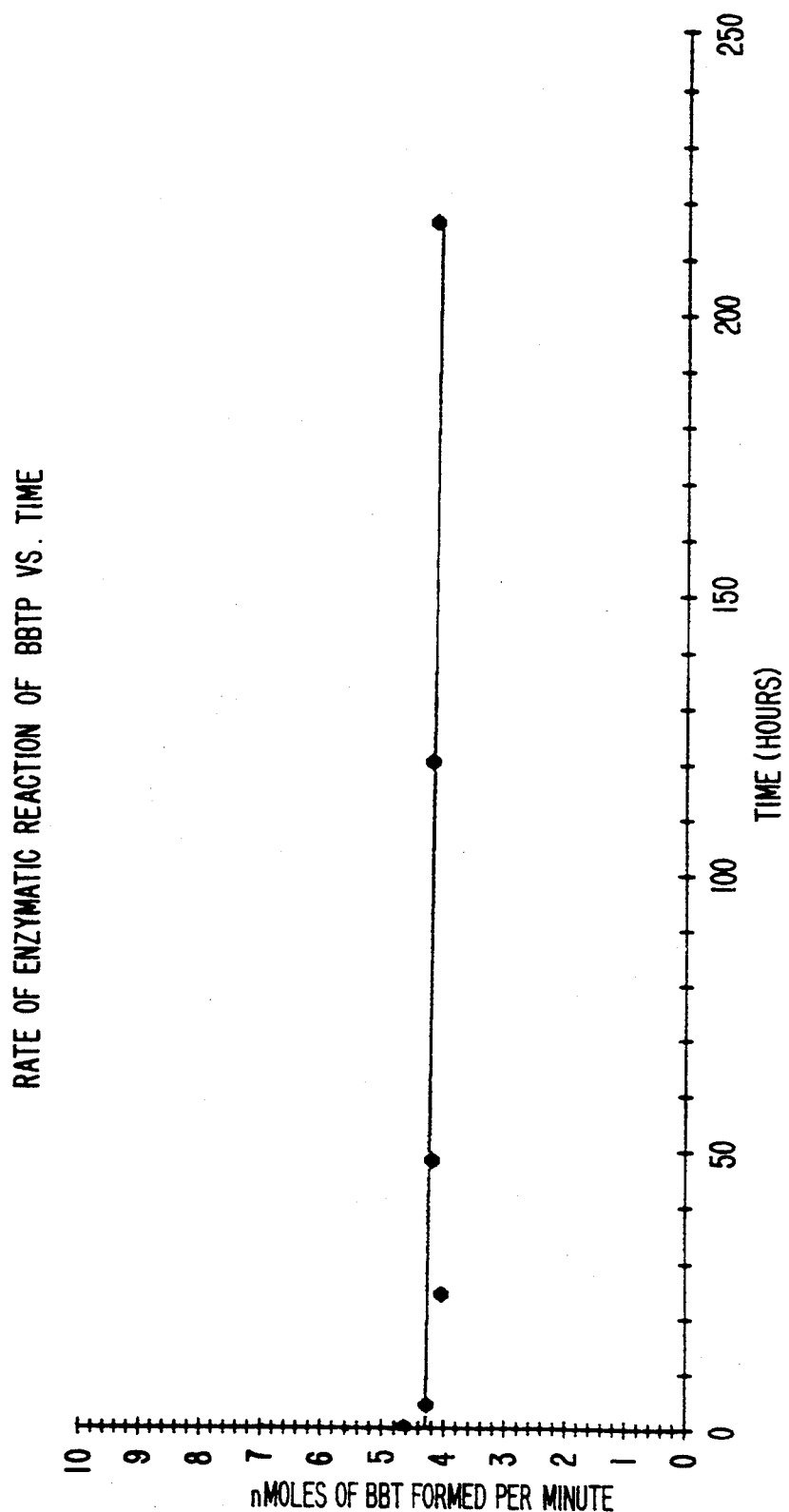
FIG. 9 is a graph of the rate of enzymatic reaction of BBTP versus time at 4° C.
Figure 10:
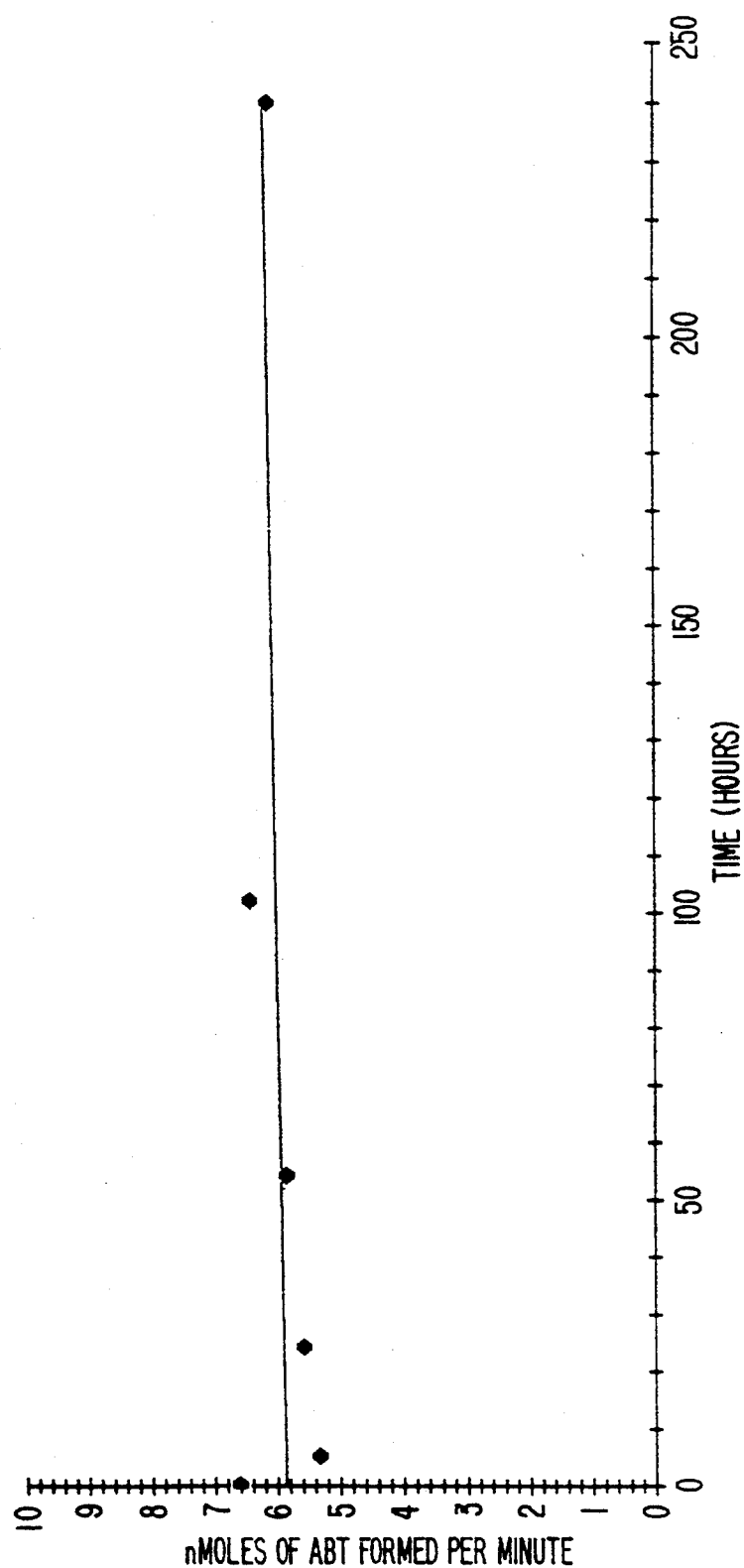
FIG. 10 is a graph of the rate of enzymatic reaction of ABTP with AP versus time at 4° C.

Next, the aqueous solutions of BBTP and ABTP were prepared and stored at 4° C. Then the rate of reaction of these solutions of BBTP and ABTP with AP were measured, see FIGS. 9 and 10 respectively. This shows that these solutions were stable and no compounds were forming which would inhibit AP. The data clearly illustrate that both BBTP and ABTP were not decomposing in solution and forming inhibitors to AP.

The procedures used in FIG. 5 could not be applied to 4-MUP for two reasons. First, the background reading obtained from a 1 mM solution was off scale on the Turner model 111. If the concentration was reduced to 0.030 mM then the background reading was comparable to a 1 mM solution of BBTP or ABTP. Since the Km for 4-MUP in this buffer is approximately 30 micromolar then the turnover of 4-MUP is reduced thus lowering the sensitivity of the substrate for AP. It was found that with freshly prepared 30 micromolar solutions of 4-MUP that it gave approximately one half to one third the signal obtained with a 1.0 mM solution of BBTP. Secondly, it was found that basic aqueous solutions of 4-MUP containing magnesium cause the 4-MUP to hydrolyze and form 4-methyl umbelliferone. This results in a significant background increase. This limits the test to having the 4-MUP being reconstituted with buffer usually within 8 hours of use even when this solution is stored at 4° C.

4. Synthesis of BT Derivatives a. Synthesis of 2-Cyano-6-Hydroxybenzothiazole (CBT)

The procedure used for the synthesis is described in Deluca, M. A. and McElroy, W. D., *Methods of Enzymology*, 57, pp. 15–24, Academic Press. The product matched the melting point and the UV data given. The HPLC showed this material to be 98% pure (by area percent). The solvent program used water for solvent A and methanol for solvent B. The flow rate was 2.0 mL/min with a program time of 10 minutes starting at 100% A to a final condition of 40% B using curve 7 on the Waters solvent programer resulting in a slightly convex solvent program. The product peak was monitored at 254 nm and found to have a retention time of 17.3 minutes. The 500 Mg hertz NMR spectra in dimethyl sulfoxide (db) verified the structure. See Table 4.

b. Synthesis of 2-cyano-6-hydroxybenzothiazole dimethyl phosphate ester.

Five hundred mg (2.84 mmoles) of 2-cyano-6-hydroxybenzothiazole was placed in a 10 mL reactor vial, which could be sealed with a teflon cap and had a magnetic stir bar. A 5.0 mL aliquot of THF was added and upon stirring the 2-CBT dissolved rapidly giving a clear, light red solution. This was followed by the addition of 0.550 mL (402 mg. 3.97 mmoles) of triethylamine. The resulting clear solution was cooled to 4° C. by placing it in an ice bath. Next, 512 mg (3.54 mmoles) of dimethylchlorophosphate dissolved in 1.5 mL of THF was added to this solution over a period of 60 seconds. After approximately 20 minutes, the 10 mL reactor vial was removed from the ice bath and allowed to stir for two hours at room temperature.

At this point the reaction was a thick slurry. The triethylammonium chloride salt was removed by suction filtration. The filtrate was transferred to a round-bottomed flask and concentrated on a rotoevaporator under vacuum. The residue was dissolved in 50 mL of ethyl acetate followed by the addition of 20 mL of water plus 10 mL of water saturated with NaCl. The phases were separated and the ethyl acetate layer was saved. The aqueous phase was back washed with 40 mL of ethyl acetate and this was combined with the previous ethyl acetate layer. The combined ethyl acetate solution was washed twice with a mixture of 15 mL of aqueous saturated NaCl and 5 mL of water. The ethyl acetate layer was dried over $MgSO_4$, filtered and concentrated on a roto-evaporator at full vacuum. Approximately 5 mL of ethyl ether was added to the concentrate which dissolved the thick oil. This was cooled to $-20°$ C. and white crystals formed rapidly. The white crystals were isolated by filtration. The melting point of the product, 2-cyano-6-hydroxybenzothiazole dimethylphosphate ester, (6-CBT-DMP) was 54.0°–55.1° C. The HPLC showed a purity of 96.4% (by area). The column was 3.9 mm×25 mm with a flow rate of 1.0 mL/min with a linear program from 100% water to 100% methanol with a program time of 30 minutes. The product was monitored at 254 nm. The retention time for the product was 23.4 minutes. The NMR spectrum was determined. The solvent used for the NMR was deuterochloroform with TMS as an internal standard. There was a doublet centered at delta 3.9 with a coupling constant of 10 Hz and integrated for 6.00H's. There was a multiplet centered at 7.9 which integrated for 3.08 hours.

c. Synthesis of 2-Carbamyl-6-Hydroxybenzothiazole (ABT)

CBT, 14.0 g or 0.079 moles, was suspended in 60 mLs of deionized water. The pH of this solution was adjusted to 11.5 using approximately 12 mLs of 6.0M sodium hydroxide. This resulted in clear dark amber solution which was left stirring overnight under nitrogen. An HPLC, 30 minute program from water to methanol with a linear program, was run the next morning. It was found that 95% (by area) of the starting material was converted to a single compound. The retention time of CBT and ABT were 15.1 and 13.2 minutes respectively.

The product was isolated by adding an equal volume of water and lowering the pH to 1.9 with 6N hydrochloric acid. The brown solids were rinsed with water. The wet solids were dissolved in 400 mLs of methanol at 60° C., hot filtered and cooled to $-15°$ C. overnight. The crystals were collected by vacuum filtration, rinsed with methanol, diethyl ether and vacuum dried. The HPLC showed a single peak at 13.2 minutes. The yield was 7.58 g or 49%. The 500 Mg hertz NMR run in DMSO-d6 is shown at Table 5. Note that the peaks at 7.910 and 8.297 were assigned to the amide hydrogens and the peak at 10.106 to the phenol hydrogen. All these peaks (7.910, 8.297 and 10.106) disappeared with the addition of deterium oxide. This is as expected for an amide. The NMR matched what was expected for the product shown.

ABT treated longer with pH 11 in aqueous solution or at a higher pH, formed 2-carboxyl-6-hydroxybenzothiazole which was, isolated, and identified. The NMR spectra matched what was obtained. This compound was also highly fluorescence with its expectedly large Stokes' shift and reacted with AP in an aqueous basic environment. This compound showed a lower turnover number with AP and was not studied extensively.

d. Synthesis of 2-Carbamyl-6-Hydroxybenzothiazole Dimethylphosphate

Three grams (0.015moles) of 2-carbamyl-6-hydroxybenzothiazole (ABT) was dissolved in 30 mLs of THF. Then 1.72 g (0.017 moles) triethylamine was added to the stirring reaction solution, followed immediately by the addition over 5 minutes of 2.6 g (0.018 moles) of dimethylchlorophosphate dissolved in 7 mLs of THF. This solution was stirred for 72 hours at room temperature.

The slurry was suction filtered and concentrated under vacuum to dryness. The solids were dissolved in 100 mLs of chloroform, washed 3 times with aqueous sodium carbonate solution, twice with saturated sodium chloride, dried over magnesium sulfate and concentrated to dryness under vacuum. The solids were slurried with diethyl ether and filtered. The yield was 1 g or 22%. The HPLC was run using a 10 minute linear program from water to methanol. It showed that the product was 96% pure (by area), with a retention time of 14.1 minutes. The NMR in deuterochloroform showed the expected peaks as follows for the product: $\delta$ of 3.9 with a coupling constant of 10 hz (6.4H), $\delta$ of at 7.6, coupling constants of 10 and 2 hz (.9H), broad peak at 8.0 (1.0H), and a doublet at 8.25 coupling constant of 10 hz (1.0H).

e. Synthesis of 2-Carbamyl-6-Hydroxybenzothiazole Phosphate Di- (2-Amino-2-Methyl-1,3-Propanediol) Salt One gram (0.0033moles) of 2-carbamyl-6-hydroxybenzothiazole dimethylphosphate was dissolve in 20 mLs of THF. To this solution, trimethylbromosilane (0.0264 moles) was added. This solution was maintained sealed in a reactor vial at room temperature for 12 hours. By HPLC there was 4% starting material and 21% monomethyl phosphate remaining after 12 hours. Another 0.0066 moles of trimethylbromosilane was added and an HPLC showed after an additional five hours that the reaction was not complete. Thus, another 0.0132 moles of trimethyl bromosilane and four more hours completed the reaction.

The vial contents were poured into 30 mLs of methanol containing 5.9 g of AMPD. The solution turned cloudy immediately and was transferred to the freezer for 18 hours. The product was collected by suction filtration, washed with cooled methanol and vacuum dried. The yield of yellow crystals was 0.98 g or 62%. An HPLC scan using a 10 minute linear program from water to methanol showed a single peak at 6.1 minutes which was 99.1% (by area percent). The 500 Mg hertz NMR spectra in deterium oxide verified the structure assignment. See Table 6.

f. Synthesis of 2'-(2-Benzothiazolyl-6'-Hydroxybenzothiazole Phosphate Bis-(2-Amino-2-Methyl-1,3-Propanediol) Salt The CBTP-bis-AMPD salts, 2.0 g or 0.0043 moles, was dissolved in 10 mLs of deionized water in a 30 mL beaker. The 2-amino-thiophenol, 0.54 g or 0.0043 moles, was dissolved in 10 mLs of methanol and added all at once to the aqueous solution. The beaker was covered with parafilm and stirred at RT for 2 hours then stored in the freezer overnight.

The solids were collected the next morning and rinsed with methanol and diethyl ether. These crude crystals were dried giving 1.1 g with a purity of 96.4% by HPLC. The crude product was purified by slurrying with a mixture of water/methanol (50/50 volume) for 20 hours followed by vacuum filtration, rinsing with water and methanol and vacuum drying. The product weighed 0.81 g and was 98.6% by HPLC analysis (area percent) with a retention time of 15.3 minutes. The program used a 5 minute linear program, 0 to 100% solvent B, starting with Solution A and finishing with methanol. The 500 Mg hertz NMR spectra in deterium oxide verified the structure. See Table 7.

The product, 100 mg, was dissolved in 10 mLs of an aqueous solution containing 0.1M AMPD, pH 10.0, with 1.0 mM magnesium chloride. At this point, a hand held 254 nm light source was used to excite a small portion the solution which had been transferred to a quartz UV cell. The solution gave off very faint blue fluorescence. Then 100 microliters of AP, 0.30 micromolar, was added. A small portion was added to the quartz UV cell and excited as before and a very bright orange fluorescence was seen. By the following morning an HPLC showed that all the CBTP-bis-AMPD had been consumed and a new peak formed in the HPLC scan. This peak was identified as 2'-(2-Benzothiazolyl)-6-Hydroxybenzothiazole (BBT) by 500 Mg hertz NMR spectra. See Table 8.

The invention may be embodied in other specific forms, including homologs and derivatives of the described compounds, without departing from the spirit or essential characteristics thereof. The present embodiment is to be considered in all respects as illustrative and not restrictive, the scope of the invention being indicated by the appended claims.

TABLE 1

FLUORESCENCE PROPERTIES OF CBT, ABT, and BBT

| | Extinction Coefficient (nm) | Excitation Maximum(nm) | Emission Maximum(nm) | Stokes Shift(nm) |
|---|---|---|---|---|
| CBT | 378 | 381 (320–430) | 510 (445–580) | 129 |
| ABT | 468 | 481 (325–440) | 518 (445–580) | 137 |
| BBT | 415 | 419 (330–480) | 561 (460–660) | 142 |
| 4-MU | N/A | Approx. 380 | 449 | 82 |

TABLE 2

Comparison of the Fluorescence Properties of CBTP to CBT

| | Voltage (volts) | Excitation Max. (nm) | Emission (nm) | Fluorescence cycles per second |
|---|---|---|---|---|
| CBTP | 700 | 377 | 504 | 53,000 |
| CBT | 700 | 378 | 501 | Off Scale (8,080,000) |
| CBT | 500 | 378 | 501 | 808,000 |

TABLE 3

Fluorescence of CBT in different solvents with and without base

| Solvent | CA absent | 10 l CA added Solution #1 | 100 l CA added Solution #2 |
|---|---|---|---|
| Aqueous 0.10 M AMPD pH 10.2 | bright green | — | — |
| Methanol | light green | bright green | bright green |
| Dimethylformamide | slight green | pale green | bright green |
| Ethanol | colorless | light green | bright green |
| Propanol | pale green | bright green | bright green |
| Acetone | colorless | colorless | light green |
| Tetrahydrofuran | colorless | colorless | pale green |
| Toluene | colorless | colorless | slight green |
| Ethyl Ether | colorless | colorless | slight blue |

TABLE 4

500 Mg Hertz NMR SPECTRA of CBT

| Chemical Shift | Integration | Coupling Constant (Hz) |
|---|---|---|
| 10.518 (S) | 0.65 | |
| 7.589 (D) | 0.88 | 2.5 |
| 7.183 (DD) | 1.09 | 9, 2.5 |
| 8.064 (D) | 1.00 | 9 |

TABLE 5

500 Mg Hertz NMR SPECTRA of ABT

| Chemical Shift | Integration | Coupling Constant (Hz) |
|---|---|---|
| 10.106 | 0.68 | |
| 8.297 (S) | 0.86 | |
| 7.910 (D) (S)* | 1.91 | 9.0 |
| 7.448 (D) | 1.00 | 2.5 |
| 7.075 (DD) | 1.14 | 9, 2.5 |

*Upon addition of H$_2$O, one of the hydrogens disappears leaving the doublet at 7.910.

TABLE 6

500 Mg Hertz NMR SPECTRA of ABTP

| Chemical Shift | Integration | Coupling Constant (Hz) |
|---|---|---|
| 8.040 (D) | 0.98 | 9.0 |

TABLE 6-continued

500 Mg Hertz NMR SPECTRA of ABTP

| Chemical Shift | Integration | Coupling Constant (Hz) |
|---|---|---|
| 7.856 (S) | 1.03 | |
| 7.468 (D) | 1.00 | 9.0 |
| 3.335 (Q) | 8.30 | 11.0 |
| 1.017 (S) | 6.00 | |

TABLE 7

500 Mg Hertz NMR SPECTRA of CBTP

| Chemical Shift | Integration | Coupling Constant (Hz) |
|---|---|---|
| 7.960 (D) | 0.60 | 2.0 |
| 7.430 (DD) | 1.00 | 2.5, 9.0 |
| 8.057 (D) | 0.95 | 9.0 |
| 8.186 (D) | 1.00 | 8.0 |
| 8.228 (D) | 1.00 | 8.0 |
| 7.610 (D,D,D)* | 1.10 | 1.5, 8.5, 7.0 |
| 7.670 (D,D,D)* | 1.15 | 1.5, 8.0, 7.0 |
| 3.335 (Q) | 8.46 | 11.0 |
| 1.017 (S) | 6.00 | |

*Appears as two triplets.

TABLE 8

500 Mg Hertz NMR SPECTRA of BBT

| Chemical Shift | Integration | Coupling Constant (Hz) |
|---|---|---|
| 7.509 (D) | 0.82 | 2.5 |
| 7.095 (DD) | 1.00 | 2.5, 8.5 |
| 7.999 (D) | 0.94 | 8.5 |
| 8.158 (D) | 1.00 | 7.5 |
| 8.224 (D) | 1.00 | 7.5 |
| 7.57 (D,D,D)* | 1.06 | 6, 6.5, 1.5 |
| 7.61 (D,D,D)* | 1.06 | 6, 6.5, 1.5 |

*Appears as two triplets.

We claim:

1. A compound for detection of enzymatic activity of a selected enzyme of the formula:

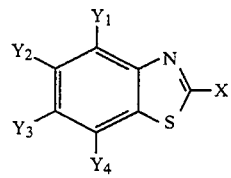

wherein:

(a) at least one of $Y_1$, $Y_2$, $Y_3$, and $Y_4$ is —A—W and the remainder are hydrogen where A is an ionizable anion group and W is a fluorescence inhibiting group and A and W are linked by a bond cleavable by said selected enzyme; and (b) X is a chemical moiety comprised of at least two atoms which extends the resonance of the benzothiazole ring with the proviso that X is not optionally substituted thiazolyl;

which compound is substantially non-fluorescent and whereby cleavage of the bond between the anion group and the fluorescence inhibiting group by the enzyme gives a reaction product which is strongly fluorescent.

2. A compound according to claim 1 wherein said enzyme is selected from the group consisting of alkaline phosphatase, choline esterase, cholesterol esterase or a lipase.

3. A compound according to claim 2 wherein said enzyme is alkaline phosphatase.

4. A compound according to claim 3 wherein —A—W is —O—P(O) (OH)$_2$.

5. A compound according to claim 4 wherein $Y_3$ is —O—P(O)(OH)$_2$ and $Y_1$, $Y_2$ and $Y_4$ are hydrogen.

6. A compound according to claim 5 wherein X is selected from the group consisting of cyano, carbamoyl and 2-benzothiazolyl.

7. A compound according to claim 6 wherein X is 2-benzothiazolyl.

8. A compound according to claim 1 herein —A—W is —O—P(O) (OH)$_2$.

9. A compound according to claim 1 wherein X is selected from the group consisting of cyano, carbamoyl and 2-benzothiazolyl.

10. A compound according to claim 1 wherein X is 2-benzothiazolyl.

11. A compound according to claim 10 wherein —A—W is —O—P(O) (OH)$_2$.

12. A compound according to claim 11 wherein $Y_3$ is —O—P(O) (OH)$_2$ and $Y_1$, $Y_2$ and $Y_4$ are hydrogen.

* * * * *